(12) United States Patent
Inaba et al.

(10) Patent No.: US 6,194,589 B1
(45) Date of Patent: Feb. 27, 2001

(54) PRODUCTION OF AMIDE DERIVATIVES AND INTERMEDIATE COMPOUNDS THEREFOR

(75) Inventors: Takashi Inaba; Yasuki Yamada, both of Takatsuki (JP)

(73) Assignees: Japan Tobacco Inc., Tokyo (JP); Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/458,004

(22) Filed: Dec. 10, 1999

Related U.S. Application Data

(62) Division of application No. 09/266,837, filed on Mar. 12, 1999, now Pat. No. 6,018,066, which is a division of application No. 09/057,710, filed on Mar. 25, 1998, now Pat. No. 5,962,704, which is a continuation of application No. PCT/JP96/02757, filed on Sep. 24, 1996.

(30) Foreign Application Priority Data

Sep. 26, 1995 (JP) .................................. 7-248184

(51) Int. Cl.⁷ .................................. C07D 321/06

(52) U.S. Cl. .......................... 549/347; 549/333

(58) Field of Search ................... 549/333, 347

(56) References Cited

U.S. PATENT DOCUMENTS

| 4,341,756 | * | 7/1982 | Sovak et al. | 424/5 |
| 4,570,007 | | 2/1986 | Niedballa et al. | 549/451 |
| 5,698,739 | * | 12/1997 | Sovak | 564/153 |

FOREIGN PATENT DOCUMENTS

| 668274 | * | 8/1995 | (EP) | C07D/321/06 |

OTHER PUBLICATIONS

Dequeker et al., Tetrahedron, vol. 51, No. 20, pp. 5877–5890, May 15, 1995.
Fuji et al., Heterocycles, vol. 42, No. 2, pp. 701–722, 1996.
Gravier–Pelletier et al., J. Carbohydr. Chem., vol. 16, No. 2, pp. 129–141, Feb. 1997.
Carreaux et al., Synlett, vol. 6, Jun. 1992, pp. 527–529.
Rao et al., CA 99: 175451, 1983.*
Sovak, CA 115: 49124, 1991.*

* cited by examiner

*Primary Examiner*—Laura L. Stockton
(74) *Attorney, Agent, or Firm*—Wenderoth, Lind & Ponack, L.L.P.

(57) ABSTRACT

A method for producing an amide derivative of the formula [XV]

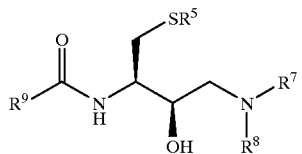

[XV]

wherein each symbol is as defined in the specification, and an enantiomer thereof, a novel intermediate useful for producing said compound and a production method thereof.

The production method of the present invention is extremely easy and simple as compared to the conventional methods, and enables effective production of compound [XV] at high yields, which includes compound [XVI] having an HIV protease inhibitory action. In addition, the novel intermediates of the present invention are extremely useful as intermediates for producing not only the aforementioned compound [XVI] but also compounds useful as X-ray contrast media.

1 Claim, No Drawings

PRODUCTION OF AMIDE DERIVATIVES AND INTERMEDIATE COMPOUNDS THEREFOR

This application is a divisional application of Ser. No. 09/266,837 filed Mar. 12, 1999 now U.S. Pat. No. 6,018,066 which is a divisional application of Ser. No. 09/057,710 filed Mar. 25, 1998 now U.S. Pat. No. 5,962,704 which is a continuation of PCT/JP96/02757, filed Sep. 24, 1996.

TECHNICAL FIELD

The present invention relates to a novel method for producing a compound of the formula [XVI]

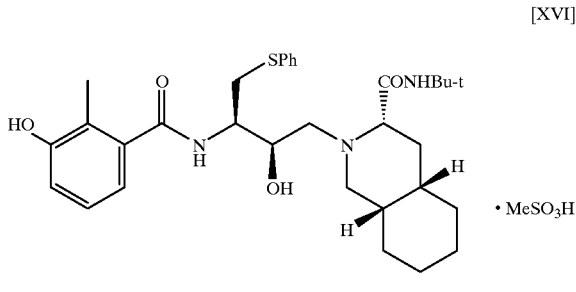

[XVI]

wherein Me is methyl, Bu-t is t-butyl and Ph is phenyl, which is useful as a treatment drug of HIV-related diseases as a result of its inhibitory action on proteases derived from viruses, various novel intermediate compounds useful for producing said compound [XVI], and to the method for production thereof. These intermediate compounds can be used not only for the production of the above-mentioned compound [XVI] but also for the production of various other compounds.

BACKGROUND ART

The above-mentioned compound [XVI] useful as an HIV protease inhibitor is known as described in WO95/09843. This compound [XVI] has been conventionally produced from serine as a starting material by increasing carbon and through numerous other steps inclusive of stereoselective reduction of carbonyl group. Such conventional production method is extremely complicated and inefficient, since it requires expensive starting materials and constant low temperature conditions for reactions. Accordingly, there remain many problems to be solved before the conventional synthetic method is actually put to industrial practice.

In addition, 2,2-dimethyl-6-amino-1,3-dioxepan-5-ol which is described in, for example, U.S. Pat. No. 4,439,613 is an intermediate for producing a compound useful as an X ray contrast medium, and even though the compound obtained is a racemate, resolution of the racemate itself by a method such as recrystallization has been extremely difficult. Moreover, this US patent does not suggest production of a specific enantiomer of the present invention.

Accordingly, an object of the present invention is to provide a method for stereoselectively and extremely efficiently producing the above-mentioned compound [XVI] useful as an HIV protease inhibitor upon solution of the above-mentioned problems. Another object of the present invention is to provide a novel intermediate compound useful for producing said compound, and a production method thereof.

DISCLOSURE OF THE INVENTION

The present inventors have made intensive studies in an attempt to achieve the above-mentioned objects, and found that a step comprising acetalating or ketalating (z)-2-butene-1,4-diol, and epoxidation of the obtained compound to give a 3,5,8-trioxabicyclo[5.1.0]octane derivative, which is followed by an epoxy ring-opening reaction using a chiral amine, leads to a stereospecific (5R,6S)-6-substituted amino-1,3-dioxepan-5-ol derivative or an enantiomer thereof, from which a compound of the following formula [XV], that is, a compound inclusive of the aforementioned compound [XVI] useful as an HIV protease inhibitor, can be extremely efficiently produced stereoselectively through various other steps, which resulted in the completion of the present invention.

That is, the present invention provides the following (1) to (14).

(1) A (5R, 6S)-6-substituted amino-1,3-dioxepan-5-ol derivative of the formula [VII]

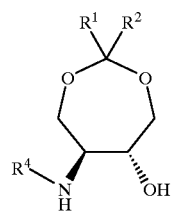

[VII]

wherein $R^1$ and $R^2$ are the same or different and each is a hydrogen atom, an alkyl or an aryl, or $R^1$ and $R^2$ combinedly form a cycloalkyl ring together with the adjacent carbon atom, and $R^4$ is an amino-protecting group, an enantiomer thereof and a salt thereof.

(2) A 1,3-dioxolan-4-yl-ethanol derivative of the formula [VIII]

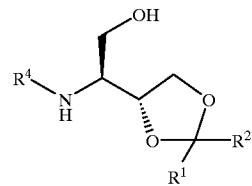

[VIII]

wherein $R^1$ and $R^2$ are the same or different and each is a hydrogen atom, an alkyl or an aryl, or $R^1$ and $R^2$ combinedly form a cycloalkyl ring together with the adjacent carbon atom, and $R^4$ is an amino-protecting group, an enantiomer thereof and a salt thereof.

(3) A method for producing a 1,3-dioxolan-4-yl-ethanol derivative of the formula [VIII]

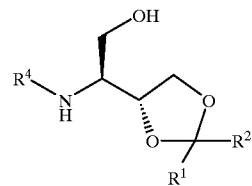

[VIII]

wherein $R^1$, $R^2$ and $R^4$ are as defined above, and an enantiomer thereof, comprising isomerizing a (5R,6S)-6-substituted amino-1,3-dioxepan-5-ol derivative of the formula [VII]

[VII]

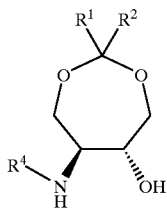

wherein $R^1$, $R^2$ and $R^4$ are as defined above, or an enantiomer thereof into a 5-membered ring in the presence of an acid.

(4) A method for producing a 1,3-dioxolan-4-yl-ethanol derivative of the formula [VIII]

[VIII]

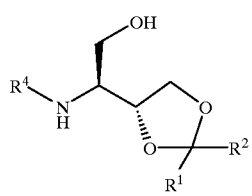

wherein $R^1$, $R^2$ and $R^4$ are as defined above, and an enantiomer thereof, comprising protecting an amino group of a (5R,6S)-6-amino-1,3-dioxepan-5-ol derivative of the formula [VI]

[VI]

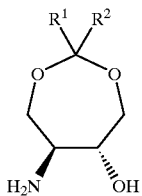

wherein $R^1$ and $R^2$ are as defined above, or an enantiomer thereof, to give a (5R,6S)-6-substituted amino-1,3-dioxepan-5-ol derivative of the formula [VII]

[VII]

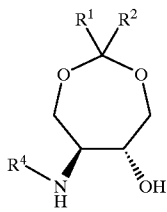

wherein $R^1$, $R^2$ and $R^4$ are as defined above, an enantiomer thereof or a salt thereof, and isomerizing the obtained compound into a 5-membered ring in the presence of an acid.

(5) A 1,3-dioxolan-4-yl-ethylthio derivative of the formula [IX]

[IX]

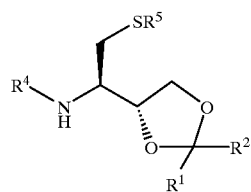

wherein $R^1$, $R^2$ and $R^4$ are as defined above, and $R^5$ is a hydrogen atop, an optionally substituted alkyl, an optionally substituted alkenyl, an optionally substituted aryl or an optionally substituted aralkyl, an enantiomer thereof and a salt thereof.

(6) A method for producing a 1,3-dioxolan-4-yl-ethylthio derivative of the formula [IX]

[IX]

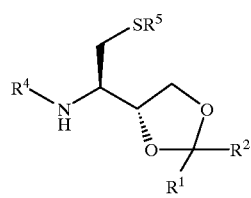

wherein $R^1$, $R^2$, $R^4$ and $R^5$ are as defined above, comprising reacting a 1,3-dioxolan-4-yl-ethanol derivative of the formula [VIII]

[VIII]

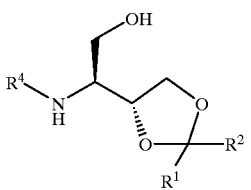

wherein $R^1$, $R^2$ and $R^4$ are as defined above, or an enantiomer thereof, with a halogenating agent or a sulfonylating agent, and reacting the obtained compound with a mercaptan of the formula $R^5SH$ wherein $R^5$ is as defined above, for thioetherification.

(7) A 3-substituted aminobutane-1,2-diol derivative of the formula [X]

[X]

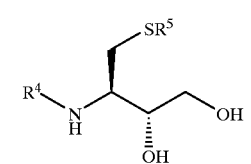

wherein $R^4$ and $R^5$ are as defined above, an enantiomer thereof and a salt thereof.

(8) A method for producing a 3-substituted aminobutane-1,2-diol derivative of the formula [X]

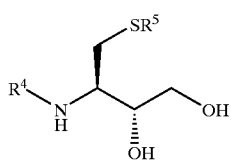

wherein $R^4$ and $R^5$ are as defined above, and an enantiomer thereof, comprising hydrolyzing a 1,3-dioxolan-4-yl-ethylthio derivative of the formula [IX]

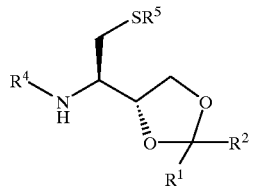

wherein $R^1$, $R^2$, $R^4$ and $R^5$ are as defined above, or an enantiomer thereof in the presence of an acid.

(9) A 3-substituted aminobutane derivative of the formula [XI]

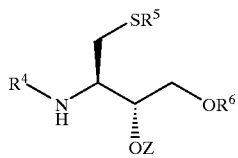

wherein $R^4$ and $R^5$ are as defined above, $R^6$ is a hydroxy-protecting group and Z is a substituent which functions as a leaving group with an oxygen atom, an enantiomer thereof and a salt thereof.

(10) A method for producing a 3-substituted aminobutane derivative of the formula [XI]

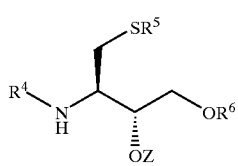

wherein $R^4$, $R^5$, $R^6$ and Z are as defined above, and an enantiomer thereof, comprising protecting a primary hydroxy of a 3-substituted aminobutane-1,2-diol derivative of the formula [X]

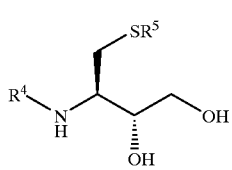

wherein $R^4$ and $R^5$ are as defined above, or an enantiomer thereof, and, with or without isolating the obtained compound, converting a secondary hydroxy to a leaving group.

(11) A substituted 1-butene oxide derivative of the formula [XII]

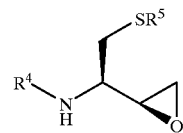

wherein $R^4$ and $R^5$ are as defined above, an enantiomer thereof and a salt thereof.

(12) A method for producing a substituted 1-butene oxide derivative of the formula [XII]

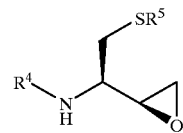

wherein $R^4$ and $R^5$ are as defined above, and an enantiomer thereof, comprising treating a 3-substituted aminobutane derivative of the formula [XI]

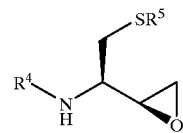

wherein $R^4$, $R^5$, $R^6$ and Z are as defined above, or an enantiomer thereof, in the presence of a base, and simultaneously conducting epoxidation and deprotection of primary hydroxy.

(13) A method for producing a substituted 1-butene oxide derivative of the formula [XII]

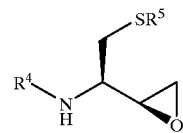

wherein $R^4$ and $R^5$ are as defined above, and an enantiomer thereof, comprising protecting a primary hydroxy of a 3-substituted aminobutane-1,2 diol derivative of the formula [X]

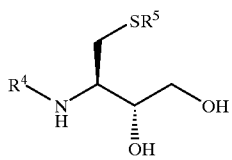

[X]

wherein R⁴ and R⁵ are as defined above, or an enantiomer thereof, converting, with or without isolating the obtained compound, a secondary hydroxy to a leaving group to give a 3-substituted aminobutane derivative of the formula [XI]

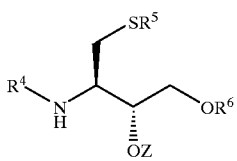

[XI]

wherein $R^4$, $R^5$, $R^6$ and Z are as defined above, or an enantiomer thereof, and treating the obtained compound in the presence of a base to simultaneously conduct epoxidation and deprotection of the primary hydroxy.

(14) A method for producing an amide derivative of the formula [XV]

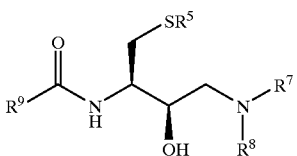

[XV]

wherein $R^5$ is as defined above, $R^7$ and $R^8$ are the same or different and each is a hydrogen atom, an optionally substituted alkyl, an optionally substituted aryl, an optionally substituted heteroaryl or an optionally substituted aralkyl, or $R^7$ and $R^8$ combinedly form a hetero ring together with the adjacent nitrogen atom, said hetero ring being optionally substituted by halogen atom, alkyl, alkenyl, alkoxy, amino, alkoxycarbonyl, carboxamide or alkyl-substituted carbamoyl, and $R^9$ is an optionally substituted alkyl, an optionally substituted aryl, an optionally substituted heteroaryl, an optionally substituted aralkyl or an optionally substituted heteroarylalkyl, and an enantiomer thereof, comprising reacting a substituted 1-butene oxide derivative of the formula [XII]

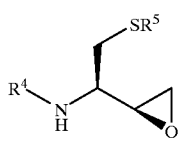

[XII]

wherein $R^4$ and $R^5$ are as defined above, or an enantiomer thereof, with an amine of the formula [XIII]

[XIII]

wherein $R^7$ and $R^8$ are as defined above, removing the amino-protecting group to give a 1,3-diamino-2-hydroxybutane derivative of the formula [XIV]

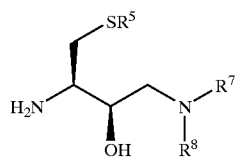

[XIV]

wherein $R^5$, $R^7$ and $R^8$ are as defined above, or an enantiomer thereof, and reacting the obtained compound with an acylating agent, followed by deprotection of the protecting group on $R^9$ where necessary.

As used herein, alkyl may be linear or branched and preferably has 1 to 6 carbon atoms. Specific examples thereof include methyl, ethyl, propyl, isopropyl, butyl, isobutyl, s-butyl, t-butyl, pentyl, isopentyl, neopentyl, t-pentyl, hexyl, isohexyl, neohexyl and the like, with preference given to lower alkyl having 1 to 4 carbon atoms such as methyl, ethyl, propyl, isopropyl, butyl, isobutyl, s-butyl and t-butyl.

The optionally substituted alkyl includes, for example, the above-mentioned alkyl which may be substituted by one or more substituent(s) which do(es) not influence the reaction. Examples of the substituents include hydroxy; halogen atoms such as fluorine, chlorine, bromine and iodine; amino; nitro; mono- or dialkylamino having 1 to 6 carbon atom(s) such as methylamino, ethylamino, hexylamino, dimethylamino and diethylamino; cyano; cycloalkyl having 3 to 7 carbon atoms such as cyclopropyl, cyclobutyl, cyclopentyl, cyclohexyl and cycloheptyl; alkoxy having 1 to 6 carbon atom(s) such as methoxy, ethoxy, propoxy, butoxy, pentyloxy and hexyloxy; carboxyl; alkoxycarbonyl having 2 to 6 carbon atoms such as methoxycarbonyl, ethoxycarbonyl, propoxycarbonyl, butoxycarbonyl and pentyloxycarbonyl; and the like. Preferred are hydroxy, halogen atom and amino.

The position and number of substituents on alkyl are not particularly limited.

The alkenyl may be linear or branched and preferably has 2 to 6 carbon atoms. Examples thereof include vinyl, allyl, crotyl, 2-pentenyl, 3-pentenyl, 2-hexenyl, 3-hexenyl, and the like, with preference given to those having 2 to 4 carbon atoms, such as vinyl, allyl and crotyl.

The optionally substituted alkenyl is that which may be substituted by one or more substituent(s) having no influence on the reaction. Examples of the substituent include those exemplified with regard to the above-mentioned optionally substituted alkyl, and the like.

The position and number of the substituents on alkenyl are not particularly limited.

The cycloalkyl ring formed by $R^1$ and $R^2$ in combination together with the adjacent carbon atom is preferably cycloalkyl ring having 3 to 7 carbon atoms, which is exemplified by cyclopropyl ring, cyclobutyl ring, cyclopentyl ring, cyclohexyl ring, cycloheptyl ring, and the like, with preference given to that having 4 to 6 carbon atoms such as cyclobutyl ring, cyclopentyl ring and cyclohexyl ring.

Examples of aryl include phenyl, naphthyl, biphenyl, and the like, with preference given to phenyl.

The optionally substituted aryl includes, for example, the above-mentioned aryl which may be substituted by one or more substituent(s) having no influence on the reaction. Examples of the substituent include those exemplified with respect to the above-mentioned optionally substituted alkyl; alkyl having 1 to 6 carbon atom(s) such as methyl, ethyl, propyl, butyl, pentyl and hexyl; alkenyl having 2 to 6 carbon atoms such as vinyl, allyl, butenyl, pentenyl and hexenyl; acyloxy having 2 to 6 carbon atoms such as acetyloxy, propionyloxy, butyryloxy, pivaloyloxy and hexanoyloxy; and the like. Preferred are alkyl, hydroxy, halogen atom, amino, nitro, alkoxy and acyloxy, and more preferred are alkyl, hydroxy, halogen atom, alkoxy and acyloxy.

While the position and number of the substituents on aryl are not particularly limited, preferred are compounds having 1 to 3 substituents and more preferred are compounds having 1 or 2 substituents.

The aryl moiety of aralkyl is exemplified by those mentioned above such as phenyl, naphthyl and biphenyl, and the like. The alkyl moiety thereof is exemplified by those mentioned above having 1 to 6 carbon atom(s), and the like. The aralkyl is exemplified by benzyl, phenethyl, phenylpropyl, phenylbutyl, phenylhexyl and the like. Preferred is aralkyl comprising phenyl with $C_1$–$C_4$ alkyl.

The optionally substituted aralkyl is that which may be substituted by one or more substituent(s) exerting no influence on the reaction. Examples of the substituent include those exemplified with respect to the aforementioned optionally substituted aryl; haloalkyl having 1 to 6 carbon atom(s) such as chloromethyl, chloroethyl and chlorobutyl; and the like. Preferred are hydroxy, halogen atom, alkyl, alkoxy, haloalkyl, nitro, acyloxy, amino and cyano. More preferred are halogen atom, alkyl, alkoxy and acyloxy. The optionally substituted aralkyl is specifically exemplified by benzyl, halogen-substituted benzyl, alkyl-substituted benzyl, alkoxy-substituted benzyl, phenethyl, halogen-substituted phenethyl, alkyl-substituted phenethyl, alkoxy-substituted phenethyl, phenylpropyl, halogen-substituted phenylpropyl, alkyl-substituted phenylpropyl, alkoxy-substituted phenylpropyl, and the like. Preferred are benzyl, phenethyl, and the like.

While the position and number of the substituents on aryl of the above-mentioned aralkyl are not particularly limited, preferred are compounds having 1 to 3 substituent(s).

Heteroaryl is, for example, pyridyl, pyrimidyl, pyrazinyl, furyl, thienyl, pyrrolyl, imidazolyl, oxazolyl, isoxazolyl, thiazolyl, isothiazolyl, indolyl, isoindolyl, quinolyl, isoquinolyl, phthalazinyl, naphthyridinyl, quinazolinyl, cinnolinyl or quinoxalinyl, with preference given to quinolyl, isoquinolyl, and the like.

The optionally substituted heteroaryl is that which may be substituted by one or more substituent(s) exerting no influence on the reaction. Examples of the substituent include those exemplified with respect to the aforementioned optionally substituted aryl. Preferred are alkyl, hydroxy, halogen atom, amino, nitro, mono- or dialkylamino, alkoxy, acyloxy, carboxyl and alkoxycarbonyl. More preferred are alkyl, hydroxy, halogen atom, mono- or dialkylamino, alkoxy and acyloxy.

While the position and number of the substituents on heteroaryl are not particularly limited, preferred are compounds having 1 to 3 substituent(s), and more preferred are compounds having 1 or 2 substituent(s).

The heteroaryl moiety of the heteroarylalkyl includes, for example, those exemplified above and the alkyl moiety includes, for example, those exemplified above having 1 to 6 carbon atom(s). Specific examples include 2-thienylmethyl, 3-furylmethyl, 4-pyridylmethyl, 2-quinolylmethyl, 3-isoquinolylmethyl and the like. Preferred is 2-quinolylmethyl.

The optionally substituted heteroarylalkyl is that which may be substituted by one or more substituent(s) exerting no influence on the reaction. Examples of the substituent include those exemplified with respect to the aforementioned optionally substituted heteroaryl, and the like.

While the position and number of the substituents on heteroaryl of the above-mentioned heteroarylalkyl are not particularly limited, preferred are compounds having 1 to 3 substituent(s).

The hetero ring to be formed by $R^7$ and $R^8$ together with the adjacent nitrogen atom is, for example, saturated or unsaturated heteroaryl having one or more nitrogen atom(s). Specific examples include imidazolyl, triazolyl, tetrazolyl, pyrrolyl, pyrrolidinyl, imidazolidinyl, hydropyridyl, piperidino, piperazinyl, oxazinyl, morpholino, azepinyl, hydroazepinyl, indolyl, hydroindolyl, isoindolyl, hydroisoindolyl, hydroquinolyl, hydroisoquinolyl, and the like. Preferred are the groups represented by the following formulas

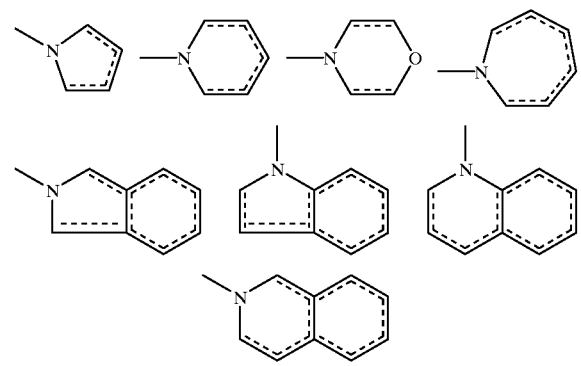

wherein the broken line may be either double bond or single bond, and more preferred is the group represented by the following formula:

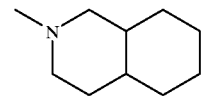

Said hetero ring may be substituted by halogen atom; alkyl having 1 to 6 carbon atom(s); alkenyl having 2 to 6 carbon atoms; alkoxy having 1 to 6 carbon atom(s); amino; alkoxycarbonyl having 2 to 6 carbon atoms; carboxamide; or alkyl-substituted carbamoyl wherein the alkyl moiety has 1 to 6 carbon atom(s).

While the position and number of substituents on the hetero ring are not particularly limited, preferred are compounds having 1 to 3 substituent(s) and more preferred are compounds having 1 or 2 substituent(s).

The halogen atom as the substituent for hetero ring includes, for example, fluorine, chlorine, bromine and iodine.

The alkyl as the substituent for hetero ring includes, for example, the aforementioned ones having 1 to 6 carbon atom(s).

The alkenyl as the substituent for hetero ring includes, for example, those mentioned above preferably having 2 to 6 carbon atoms.

The alkoxy as the substituent for hetero ring includes, for example, linear or branched alkoxy preferably having 1 to 6 carbon atom(s), which is exemplified by methoxy, ethoxy, propoxy, isopropoxy, butoxy, isobutoxy, s-butoxy, t-butoxy, pentyloxy, isopentyloxy, neopentyloxy, hexyloxy, and the like. More preferred are those having 1 to 4 carbon atom(s) such as methoxy, ethoxy, propoxy, isopropoxy and butoxy, with further preference given to those having 1 or 2 carbon atom(s) such as methoxy and ethoxy.

The alkoxycarbonyl as the substituent for hetero ring includes, for example, alkoxycarbonyl preferably having 2 to 6 carbon atoms, which is exemplified by the above-mentioned alkoxy having 1 to 5 carbon atom(s) with carbonyl group, and the like.

The alkyl-substituted carbamoyl as the substituent for hetero ring includes, for example, those wherein the alkyl moiety preferably has 1 to 6 carbon atom(s), which is exemplified by N-methylcarbamoyl, N-ethylcarbamoyl, N-propylcarbamoyl, N-t-butylcarbamoyl, N-pentylcarbamoyl, N-hexylcarbamoyl, and the like. Preferred is N-t-butylcarbamoyl.

The amino-protecting group includes, for example, optionally substituted aralkylidene such as benzylidene, 4-chlorobenzylidene, 4-nitrobenzylidene, salicylidene, α-naphthylidene and β-naphthylidene; optionally substituted aralkyl such as benzyl, 4-methoxybenzyl, 3,4-dimethoxybenzyl, 2-nitrobenzyl, 4-nitrobenzyl, benzhydryl, bis(4-methoxyphenyl)methyl and trityl; optionally substituted acyl such as formyl, acetyl, propionyl, butyryl, pivaloyl, 2-chloroacetyl, 2-bromoacetyl, 2-iodoacetyl, 2,2-dichloroacetyl, 2,2,2-trichloroacetyl, 2,2,2-trifluoroacetyl, phenylacetyl, phenoxyacetyl, benzoyl, 4-chlorobenzoyl, 4-methoxybenzoyl, 4-nitrobenzoyl, naphthylcarbonyl and adamantylcarbonyl; optionally substituted alkoxycarbonyl such as methoxycarbonyl, ethoxycarbonyl, propoxycarbonyl, isopropoxycarbonyl, t-butoxycarbonyl, pentyloxycarbonyl, isopentyloxycarbonyl, cyclohexyloxycarbonyl, 2-chloroethoxycarbonyl, 2-iodoethoxycarbonyl, 2,2,2-trichloroethoxycarbonyl, 2,2,2-trichloro-t-butoxycarbonyl, benzhydryloxycarbonyl, bis-(4-methoxyphenyl)methoxycarbonyl, phenacyloxycarbonyl, 2-trimethylsilylethoxycarbonyl, 2-triphenylsilylethoxycarbonyl and fluorenyl-9-methoxycarbonyl; optionally substituted alkenyloxycarbonyl such as vinyloxycarbonyl, 2-propenyloxycarbonyl, 2-chloro-2-propenyloxycarbonyl, 3-methoxycarbonyl-2-propenyloxycarbonyl, 2-methyl-2-propenyloxy-carbonyl, 2-butenyloxycarbonyl and cinnamyloxycarbonyl; phenoxycarbonyl; optionally substituted aralkyloxycarbonyl such as benzyloxycarbonyl, 4-bromobenzyloxycarbonyl, 2-chlorobenzyloxycarbonyl, 3-chlorobenzyloxycarbonyl, 3,5-dimethoxybenzyloxycarbonyl, 4-methoxybenzyloxycarbonyl, 2-nitrobenzyloxycarbonyl, 4-nitrobenzyloxycarbonyl, 2-nitro-4,5-dimethoxybenzyloxycarbonyl, 3,4,5-trimethoxybenzyloxycarbonyl and phenethyloxycarbonyl; optionally substituted lower alkylsilyl such as trimethylsilyl and t-butyldimethylsilyl; optionally substituted alkylthiocarbonyl such as methylthiocarbonyl, ethylthiocarbonyl, butylthiocarbonyl and t-butylthiocarbonyl; optionally substituted aralkylthiocarbonyl such as benzylthiocarbonyl; optionally substituted phosphoryl such as dicyclohexylphosphoryl, diphenylphosphoryl, dibenzylphosphoryl, di-(4-nitrobenzyl)phosphoryl and phenoxyphenylphosphoryl; and optionally substituted phosphinyl such as diethylphosphinyl and diphenylphosphinyl. It may be phthaloyl as occasion demands. Preferred is aralkyloxycarbonyl and more preferred is benzyloxycarbonyl.

Examples of hydroxy-protecting group include ether protecting groups such as methoxymethyl, methoxyethyl, tetrahydropyranyl, benzyl and trityl; silyl ether protecting groups such as trimethylsilyl and t-butyldimethylsilyl; ester protecting groups such as acetyl, pivaloyl, benzoyl, toluoyl, p-nitrobenzoyl and p-methoxybenzoyl; and the like. Preferred is ester protecting group, with more preference given to p-nitrobenzoyl.

The substituent (Z group) which functions as a leaving group together with oxygen atom includes, for example, as a group joining with oxygen atom (leaving group: OZ group), sulfonic acid derivatives such as tosyloxy (p-toluenesulfonyloxy), brosyloxy (p-bromobenzenesulfonyloxy), mesyloxy (methanesulfonyloxy), benzenesulfonyloxy, camphorsulfonyloxy and trifyloxy (trifluoromethanesulfonyloxy), with preference given to mesyloxy (methanesulfonyloxy).

Examples of salts include, but not limited to, alkali metal salts such as sodium salt, potassium salt and cesium salt; alkaline earth metal salts such as calcium salt and magnesium salt; organic amine salts such as triethylamine salt, pyridine salt, picoline salt, ethanolamine salt, triethanolamine salt, dicyclohexylamine salt and N,N'-dibenzylethylenediamine salt; inorganic acid salts such as hydrochloride, hydrobromide, sulfate and phosphate; organic acid salts such as formate, acetate, trifluoroacetate, maleate and tartrate; sulfonates such as methanesulfonate, benzenesulfonate and p-toluenesulfonate; amino acid salts such as arginine, aspartate and glutamate; and the like.

The present invention encompasses various isomers of respective compounds.

The method for producing compound [XV] from (z)-2-butene-1,4-diol which is used as a starting compound, that is, the method for producing compounds inclusive of the above-mentioned final objective compound [XVI] useful as an HIV protease inhibitor is described in detail in the following.

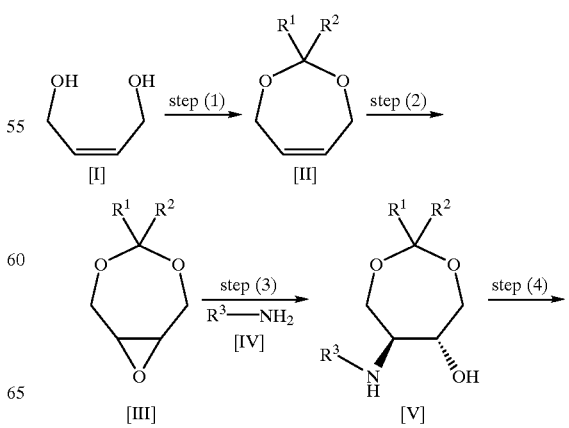

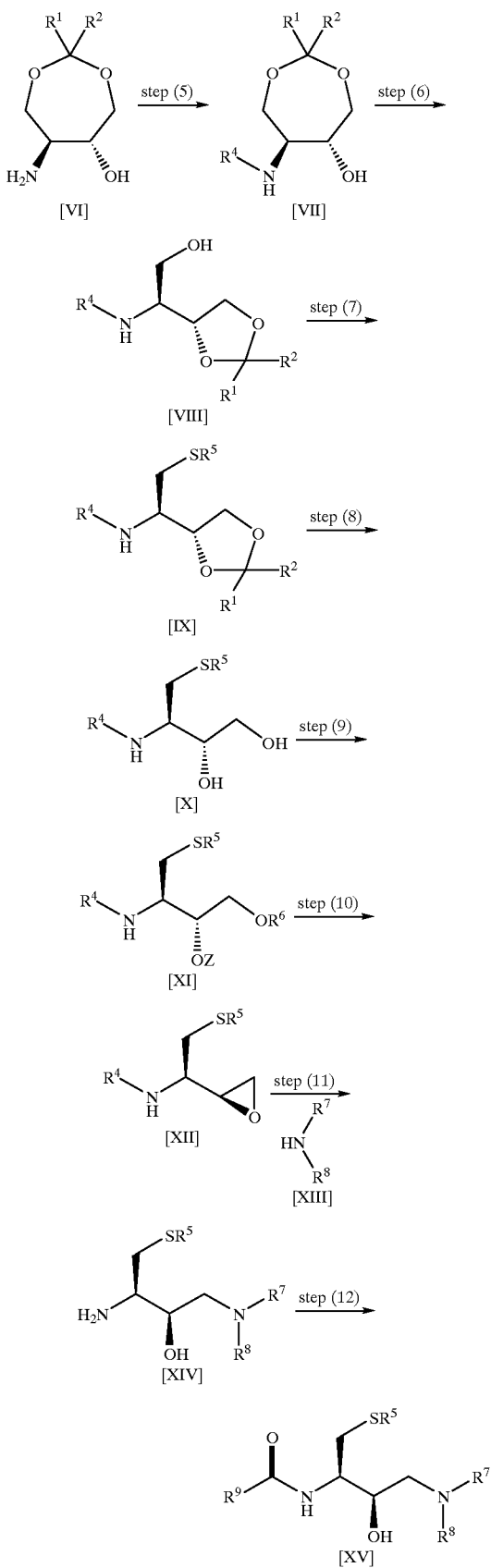

wherein $R^1$, $R^2$, $R^4$, $R^5$, $R^6$, $R^7$, $R^8$, $R^9$ and Z are as defined above and $R^3$ is aralkylamine residue or amino acid derivative residue.

Step (1): Protection of diol

The reaction per se is known wherein (z)-2-butene-1,4-diol [I] is reacted with an acetalating agent or a ketalating agent without solvent or in a suitable solvent, in the presence of a dehydrating agent or a suitable catalyst such as an acid, thereby to protect hydroxyl groups and produce compound [II].

Examples of the acetalating agent and ketalating agent include carbonyl compounds such as formaldehyde, acetaldehyde, benzaldehyde, acetone, diethyl ketone, methyl ethyl ketone, acetophenone, cyclopentanone and cyclohexanone; gem-dialkoxy compounds such as dimethoxymethane, 1,1-dimethoxyacetaldehyde, benzaldehydodimethyl-acetal, 2,2-dimethoxypropane and cyclohexanone dimethylacetal; vinyl ether compounds such as methyl vinyl ether, ethyl vinyl ether, 2-methoxypropene, 2-ethoxypropene and 1-methoxycyclohexene; and the like. Preferred are gem-dialkoxy compounds, with more preference given to 2,2-dimethoxypropane.

The catalyst is appropriately selected according to the kind of acetalating agent and ketalating agent. Suitable catalyst includes, for example, inorganic acids such as sulfuric acid, hydrochloric acid and nitric acid; and organic acids such as acetic acid, trifluoroacetic acid, methanesulfonic acid, p-toluenesulfonic acid, benzenesulfonic acid and camphorsulfonic acid. Preferred are organic acids, with more preference given to p-toluenesulfonic acid.

Examples of the dehydrating agent include phosphorus pentoxide, molecular sieves, phosphorus pentachloride, and the like. Preferred are molecular sieves.

The solvent is appropriately selected according to the kind of acetalating agent and ketalating agent. Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; and polar solvents such as N,N-dimethylformamide, dimethyl sulfoxide, acetonitrile and acetone, with preference given to hydrocarbon solvents and more preference given to a reaction without solvent.

The reaction (refluxing) temperature is suitably 0–200° C., preferably 80–160° C.

The compound [II] can be used directly in the next step without isolation.

Step (2): Epoxidation with oxidizing agent

This step comprises epoxidation of compound [II] without solvent or in a suitable solvent using an oxidizing agent to give compound [III]. Like Step (1), this reaction per se is known (see U.S. Pat. No. 4,439,613).

As the oxidizing agent, inorganic oxidizing agents such as hydrogen peroxide, Oxon (trademark); and organic oxidizing agents such as m-chloroperbenzoic acid, peracetic acid and t-butylhydroperoxide can be used. Preferred are inorganic oxidizing agents and more preferred is hydrogen peroxide. In this case, sodium hydroxide, or sodium hydroxide and disodium hydrogenphosphate in combination are desirably co-used for smooth progress of the reaction.

The solvent is appropriately selected according to the kind of oxidizing agent. Suitable solvents include, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, acetonitrile, acetone, formic acid, acetic acid and water; and mixed solvents thereof. Preferred are alcohol solvents and more preferred is a mixed solvent of methanol, acetonitrile and water.

While the reaction temperature varies depending on the oxidizing conditions, it is suitably 0–150° C. and preferably 50–100° C. The reaction time is preferably 3 to 8 hours.

The compound [III] can be used directly in the next step without isolation.

Step (3): Epoxy ring-opening reaction with chiral amine

This step comprises epoxy ring-opening of compound [III] with chiral amine [IV] of the formula: $R^3$—$NH_2$ wherein $R^3$ is as defined above, in a suitable solvent or without solvent, and subjecting the mixture of isomers thus produced to crystallization (e.g. recrystallization) to give an optically pure compound [V] or an enantiomer thereof.

The chiral amine is an amine having an asymmetric carbon atom adjacent to amino, that is, an amine having an (R) or (S) configuration, which is typically exemplified by aralkylamine, amino acid derivatives, and the like.

Examples of aralkylamine include (R)-1-phenylethylamine, (S)-1-phenylethylamine, (R)-1-(1-naphthyl)ethylamine, (S)-1-(1-naphthyl)-ethylamine, (R)-α-phenylglycinol, (S)-α-phenylglycinol, and the like. Preferred is (R)-1-phenylethylamine.

Examples of amino acid derivative include amino acids such as (R)-serine, (S)-serine, (R)-α-phenylglycine and (S)-α-phenylglycine; amino acid derivatives such as (R)-serine methyl ester, (S)-serine methyl ester, (R)-α-phenylglycine methyl ester and (S)-α-phenylglycine methyl ester, and the like. Preferred is (R)-α-phenylglycine.

Aralkylamine residue and amino acid derivative residue at $R^3$ respectively mean a group which is other than amino group and which binds to amino group in the above-mentioned aralkylamine and amino acid derivative.

By appropriately selecting the chiral amine, a compound [V] or an enantiomer of compound [V] can be obtained.

Suitable solvents to be used for the reaction include, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred are alcohol solvents and more preferred is isopropyl alcohol.

The reaction temperature is suitably 0–150° C. and preferably 50–100° C. The reaction time is preferably 20 to 30 hours.

Suitable solvents to be used for crystallization include, for example, alcohol solvents such as methanol, ethanol, n-propyl alcohol, isopropyl alcohol, n-butyl alcohol and t-butyl alcohol; hydrocarbon solvents such as benzene, toluene, hexane, heptane, methylcyclohexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile, acetone and water; and mixed solvents thereof. Preferred are hydrocarbon solvents and a mixed solvent of hydrocarbon solvent and alcohol solvent and more preferred is a mixed solvent of hexane or heptane, and isopropyl alcohol.

Step (4): Removal of chiral element

This step comprises removing chiral element ($R^3$) under suitable conditions from the compound [V] or an enantiomer thereof obtained in Step (3) to give a chiral compound [VI] or an enantiomer thereof.

The conditions of removal are appropriately determined according to the kind of chiral element. For example, when $R^3$ is 1-phenylethyl, the chiral element can be removed by catalytic reduction in a suitable solvent in the presence of a suitable catalyst such as palladium hydroxide, and hydrogen source.

In this case, suitable catalyst includes, for example, palladium catalysts (e.g., palladium hydroxide-carbon, palladium-carbon and palladium-alumina), platinum catalysts (e.g., platinum oxide), rhodium catalysts (e.g., rhodium-alumina) and ruthenium catalysts (e.g., ruthenium-alumina). Preferred are to palladium catalysts with more preference given to palladium hydroxide-carbon.

Examples of the hydrogen source include hydrogen gas, ammonium formate, formic acid, cyclohexadiene, and the like. Preferred is hydrogen gas.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, formic acid, acetic acid and water; and mixed solvents thereof. Preferred are alcohol solvents, polar solvents and a mixed solvent of alcohol solvent and polar solvent, and more preferred is a mixed solvent of isopropyl alcohol, acetic acid and water.

The reaction temperature is suitably 0–100° C. and preferably 20–60° C. The reaction time is preferably 5 to 20 hours.

Step (5): Protection of amino

This step comprises reacting compound [VI] or an enantiomer thereof obtained in Step (4), with an acid halide or acid anhydride corresponding to $R^4$ under appropriate conditions, thereby to protect the amino thereof with a protecting group ($R^4$) to obtain compound [VII] or an enantiomer thereof.

Examples of the amino-protecting group ($R^4$) include those mentioned above.

The acid halide corresponding to $R^4$ is not particularly limited as long as it corresponds to $R^4$ and exemplified by benzyloxycarbonyl. chloride, ethoxycarbonyl chloride, and the like. The acid anhydride corresponding to $R^4$ is not particularly limited as long as it corresponds to $R^4$ and exemplified by di-t-butyldicarbonate, di-(2,2,2-trichloro-t-butyl)dicarbonate, and the like.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2- dichloroethane; ester solvents such as ethyl acetate, methyl acetate and butyl acetate; polar solvents such as N,N-dimethylformamide, dimethyl sulfoxide, acetonitrile, acetone and water; and mixed solvents thereof. Preferred is a two phase solvent of ester solvent and water and more preferred is a two phase solvent of ethyl acetate and water.

The reaction temperature is suitably 0–100° C. and preferably 20–60° C. The reaction time is preferably 2 to 10 hours.

Step (6): Isomerization from 7-membered ring to 5-membered ring

This step comprises isomerizing the 7-membered ring moiety of compound [VII] or an enantiomer thereof using a suitable acid in a suitable solvent into a thermodynamically advantageous 5-membered ring structure, whereby compound [VIII] or an enantiomer thereof is obtained.

Suitable acid includes, for example, inorganic acids such as sulfuric acid, hydrochloric acid and nitric acid; and organic acids such as acetic acid, trifluoroacetic acid, methanesulfonic acid, p-toluenesulfonic acid, p-toluenesulfonic acid pyridinium, benzenesulfonic acid and camphorsulfonic acid, with preference given to organic acid and more preference given to p-toluenesulfonic acid pyridinium.

Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile and acetone; and mixed solvents thereof. Preferred is polar solvent and more preferred is acetone.

The reaction temperature is suitably 0–100° C. and preferably 20–50° C. The reaction time is preferably 2 to 6 hours.

Step (7): Thioetherification of hydroxy

This step comprises reacting compound [VIII] or an enantiomer thereof with a halogenating agent or a sulfonylating agent in a suitable solvent in the presence of a suitable base to convert the hydroxy thereof into a suitable leaving group, and, with or without isolation, reacting the obtained compound with a desired mercaptan of the formula: R$^5$SH wherein R$^5$ is as defined above, in the presence of a suitable base to give compound [IX] or an enantiomer thereof.

Suitable leaving group includes, for example, halogen such as chlorine, bromine and iodine; and sulfonyloxy such as methane-sulfonyloxy, trifluoromethanesulfonyloxy, benzenesulfonyloxy, toluenesulfonyloxy and camphorsulfonyloxy, with preference given to sulfonyloxy and more preference given to methanesulfonyloxy.

As the halogenating agent, usable are, for example, phosphorus chloride, phosphorus oxychloride, phosphorus bromide, thionyl chloride and phosphorus pentachloride.

Examples of sulfonylating agent include sulfonyl chloride such as methanesulfonyl chloride, benzenesulfonyl chloride, toluenesulfonyl chloride and camphorsulfonyl chloride; sulfonic anhydride such as methanesulfonic anhydride and trifluoromethanesulfonic anhydride, and the like. Preferred is sulfonyl chloride and more preferred is methanesulfonyl chloride.

Examples of suitable base include organic base such as pyridine, lutidine, picoline, triethylamine, diisopropylethylamine, dimethyl-aminopyridine, DBU (1,8-diazabicyclo[5.4.0]-7-undecene), DBN (1,5-diazabicyclo[4.3.0]-5-nonene), and the like. Preferred are pyridine and triethylamine, particularly triethylamine.

Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile and acetone; and mixed solvents thereof. Preferred is polar solvent and more preferred is N,N-dimethylformamide.

The desired mercaptan may be any as long as it has mercapto group, and includes, for example, optionally substituted arylmercaptans such as thiophenol and toluenethiol; optionally substituted alkylmercaptans such as methylmercaptan, ethylmercaptan, propylmercaptan, isopropylmercaptan, butylmercaptan, isobutylmercaptan, s-butylmercaptan and t-butylmercaptan; optionally substituted aralkylmercaptans such as benzylmercaptan, phenethylmercaptan and naphthylmethylmercaptan; and optionally substituted alkenylmercaptans such as vinylmercaptan and allylmercaptan. Preferred are arylmercaptans and more preferred is thiophenol.

Suitable base to be used for the reaction with desired mercaptans includes, for example, organic bases such as pyridine, lutidine, picolin, triethylamine, diisopropylethylamine, dimethylaminopyridine, DBU and DBN; and inorganic bases such as lithium hydroxide, sodium hydroxide, potassium hydroxide, sodium hydrogencarbonate, potassium hydrogencarbonate, sodium carbonate and potassium carbonate, with preference given to inorganic bases, more preferably potassium carbonate.

The reaction temperature is suitably 0–100° C. and preferably 0–50° C. The reaction time is preferably 5–20 hours.

Step (8): Removal of diol-protecting group

This step comprises hydrolyzing acetal or ketal moiety of compound [IX] or an enantiomer thereof in a suitable solvent in the presence of a suitable acid to give a diol compound [X] or an enantiomer thereof.

Suitable acid includes, for example, inorganic acids such as hydrochloric acid, sulfuric acid and nitric acid; and organic acids such as acetic acid, trifluoroacetic acid, benzenesulfonic acid, p-toluenesulfonic acid and camphorsulfonic acid, with preference given to inorganic acid and more preference given to hydrochloric acid.

Suitable solvent includes, for example, alcohol solvents such as methanol, ethanol, propyl alcohol, isopropyl alcohol, n-butyl alcohol, isobutyl alcohol, s-butyl alcohol and t-butyl alcohol; ether solvents such as diethyl ether, 1,2-dimethoxyethane, tetrahydrofuran and diglyme; polar solvents such as N,N-dimethylformamide, dimethyl sulfoxide, acetonitrile, acetone and water; and mixed solvents thereof. Preferred is alcohol solvent, and more preferred is methanol.

The reaction temperature is suitably 0–100° C. and preferably 20–80° C. The reaction time is preferably 30 minutes to 2 hours.

Step (9): Protection of primary hydroxy and conversion of secondary hydroxy to leaving group This step comprises reacting compound [X] or an enantiomer thereof with an acid halilde or acid anhydride corresponding to R$^6$ in a suitable solvent in the presence of a base to protect the primary hydroxy thereof with a protecting group R$^6$, and, with or without isolation, reacting the obtained compound with a sulfonylating agent to convert the secondary hydroxy to a leaving group (OZ), whereby compound [XI] or an enantiomer thereof is obtained.

Suitable base includes, for example, organic base such as pyridine, lutidine, picoline, triethylamine, diisopropylethylamine, dimethylaminopyridine, DBU and DBN; and inorganic base such as lithium hydroxide, sodium hydroxide, potassium hydroxide, sodium hydrogencarbonate, sodium carbonate and potassium carbonate, with preference given to organic base, particularly triethylamine.

Suitable solvent includes, for example, hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile and acetone; and mixed solvents thereof. Preferred is ether solvent and more preferred is tetrahydrofuran.

The hydroxy-protecting group ($R^6$) includes those exemplified above.

The agent for introducing protecting group is, for example, acid halide or acid anhydride corresponding to $R^6$, which is appropriately selected according to the kind of the protecting group. For example, anhydride or acid chloride of the corresponding carboxylic acid is used in the case of ester protecting group, which is preferably exemplified by p-nitrobenzoyl chloride.

Examples of the leaving group (OZ) include, as mentioned above, sulfonic acid derivatives such as tosyloxy (p-toluenesulfonyloxy), brosyloxy (p-bromobenzenesulfonyloxy), mesyloxy (methanesulfonyloxy), benzenesulfonyloxy, camphorsulfonyloxy, triphiloxy (trifluoromethane-sulfonyloxy), and the like. Preferred is mesyloxy (methanesulfonyloxy) .

Examples of suitable sulfonylating agent include sulfonyl chloride such as methanesulfonyl chloride, benzenesulfonyl chloride, toluenesulfonyl chloride and camphorsulfonyl chloride, sulfonic anhydride such as methanesulfonic anhydride and trifluoromethane-sulfonic anhydride, and the like. Preferred is sulfonyl chloride, and more preferred is methanesulfonyl chloride.

The reaction temperature is suitably 0–20° C. and preferably 0–10° C. The reaction time is preferably 1 to 5 hours.

Step (10): Epoxidation

This step comprises treating compound [XI] or an enantiomer thereof with a suitable base in a suitable solvent to simultaneously carry out deprotection of primary hydroxy and epoxidation, thereby to introduce compound [XII] or an enantiomer thereof.

Suitable base includes, for example, inorganic bases such as lithium hydroxide, sodium hydroxide, potassium hydroxide, calcium hydroxide, barium hydroxide, sodium carbonate, potassium carbonate, sodium hydrogencarbonate and calcium carbonate; and organic bases such as alkoxides (e.g., sodium methoxide, sodium ethoxide and potassium t-butoxide), with preference given to inorganic base, particularly potassium hydroxide.

Suitable solvent is appropriately selected according to the base to be used. Examples thereof include alcohol solvents such as methanol, ethanol, n-propyl alcohol, isopropyl alcohol, n-butyl alcohol and t-butyl alcohol; ether solvents such as diethyl ether, 1,2-dimethoxyethane, tetrahydrofuran, diglyme and 1,4-dioxane; polar solvents such as N,N-dimethylformamide, dimethyl sulfoxide, acetonitrile, acetone and water; mixed solvents thereof; and the like. Preferred is a mixed solvent of ether solvent and water, and more preferred is a mixed solvent of 1,4-dioxane and water.

The reaction temperature is suitably 0–30° C. and preferably 0–20° C. The reaction time is preferably 30 minutes to 5 hours.

Step (11): Epoxy ring opening with amine and removal of amino-protecting group

This step comprises treating compound [XII] or an enantiomer thereof with amine [XIII] in a suitable solvent to open epoxy ring and, with or without isolation, removing amino-protecting group ($R^4$) to give compound [XIV] or an enantiomer thereof.

The amine may be any as long as it has at least one hydrogen atom on nitrogen, and is exemplified by ammonia, methylamine, ethylamine, propylamine, isopropylamine, aniline, anisidine, dimethylamine, diethylamine, dipropylamine, diisopropylamine, methylethylamine, methylisopropylamine, methylaniline, pyrrolidine, piperidine, decahydroisoquinoline, (3S, 4aS, 8aS)-decahydroisoquinoline-3-carboxylic acid t-butylamide, and the like.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; polar solvents such as N,N-dimethylformamide, dimethyl sulfoxide, acetonitrile, acetone and water; and mixed solvents thereof. Preferred is alcohol solvent, and more preferred is isopropyl alcohol.

The reaction temperature of ring opening with amine is suitably 0–100° C. and preferably 50–80° C. The reaction time is preferably 1 to 10 hours.

The method for eliminating amino-protecting group ($R^4$) can be suitably selected according to the kind of the protecting group. When the protecting group is a carbamate such as t-butoxycarbonyl and benzyloxycarbonyl, for example, the compound is treated with a suitable base in a suitable solvent for deprotection.

Suitable base includes, for example, inorganic bases such as lithium hydroxide, sodium hydroxide, potassium hydroxide, calcium hydroxide, barium hydroxide, sodium carbonate, potassium carbonate, sodium hydrogencarbonate and calcium carbonate; and organic bases such as alkoxides (e.g., sodium methoxide, sodium ethoxide and potassium t-butoxide), ammonia, methylamine, ethylamine, dimethylamine and diethylamine, with preference given to inorganic base, particularly potassium hydroxide.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; polar solvents such as N,N-dimethylformamide, dimethyl sulfoxide, acetonitrile, acetone and water; and mixed solvents thereof. Preferred is a mixed solvent of alcohol solvent and water, and more preferred is a mixed solvent of isopropyl alcohol and water.

The reaction temperature is suitably 0–100° C. and preferably 50–80° C. The reaction time is preferably 5 to 20 hours.

Step (12): Modification of amino

This step comprises acylating the amino group of compound [XIV] or an enantiomer thereof with a desirable acylating agent in a suitable solvent in the presence of a base and, where necessary, removing the protecting group on $R^9$ to give compound [XV] or an enantiomer thereof.

Suitable base includes, for example, organic bases such as pyridine, lutidine, picoline, triethylamine, diisopropylethylamine, dimethylaminopyridine, DBU and DBN; and inorganic bases such as lithium hydroxide, sodium hydroxide, potassium hydroxide, sodium hydrogencarbonate, sodium carbonate and potassium carbonate, with preference given to inorganic base, particularly sodium hydrogencarbonate.

The acylating agent may be any as long as it reacts with primary amino, and is exemplified by optionally substituted alkylcarboxylic anhydrides such as acetic anhydride and pivalic anhydride; optionally substituted arylcarboxylic anhydrides such as benzoic anhydride and toluic anhydride; optionally substituted alkylcarbonyl chlorides such as acetyl chloride and pivaloyl chloride; optionally substituted arylcarbonyl chlorides such as benzoyl chloride and toluoyl chloride; optionally substituted heteroarylcarboxylic anhydrides and optionally substituted heteroarylcarbonyl chlorides; optionally substituted aralkylcarboxylic anhydrides and optionally substituted aralkyl-carbonyl chlorides; optionally substituted heteroarylalkylcarboxylic anhydrides and optionally substituted heteroarylalkylcarbonyl chlorides; and the like. In addition, an acid chloride having a protecting group, such as 3-acetoxy-2-methylbenzoyl chloride can be used.

Suitable solvent is appropriately selected according to the kind of the base to be used. Examples thereof include alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethyl-formamide, dimethyl sulfoxide, acetonitrile, acetone and water; mixed solvents thereof; and the like. Preferred is a two phase solvent of ester solvent and water and more preferred is a two phase solvent of ethyl acetate and water.

The reaction temperature is suitably 0–20° C. and preferably 0–10° C. The reaction time is preferably 30 minutes to 3 hours.

When the above-mentioned acylating agent has a protecting group, such protecting group may be eliminated.

The method for deprotection is appropriately selected according to the kind of the protecting group. For example, when 3-acetoxy-2-methylbenzoyl chloride is used as an acylating agent, the acetyl group as the protecting group can be removed by treating the compound with a suitable base in a suitable solvent.

Examples of protecting group include acetyl, pivaloyl, benzoyl, trichloroacetyl, trifluoroacetyl, and the like.

Suitable base includes, for example, organic bases such as amines (e.g., ammonia, methylamine, ethylamine, dimethylamine and diethylamine); and inorganic bases such as lithium hydroxide, sodium hydroxide, potassium hydroxide, sodium hydrogencarbonate, sodium carbonate and potassium carbonate, with preference given to amines, particularly ammonia.

Suitable solvent includes, for example, alcohol solvents such as methanol, ethanol, n-propyl alcohol, isopropyl alcohol, n-butyl alcohol and t-butyl alcohol; hydrocarbon solvents such as benzene, toluene, hexane and xylene; ether solvents such as diethyl ether, 1,2-dimethoxyethane, tetrahydrofuran and diglyme; halogen solvents such as dichloromethane, chloroform, carbon tetrachloride and 1,2-dichloroethane; ester solvents such as ethyl acetate, methyl acetate and butyl acetate; polar solvents such as N,N-dimethylformamide, dimethyl sulfoxide, acetonitrile, acetone and water; and mixed solvents thereof. Preferred is alcohol solvent and more preferred is methanol.

The reaction temperature is suitably 0–100° C. and preferably 20–50° C. The reaction time is preferably 1 to 5 hours.

The enantiomers of the above-mentioned compound [XV] and various intermediates can be obtained by the same reactions as above using an enantiomer of compound [V] obtained in Step (3).

The compound [XV], various intermediates and enantiomers thereof can be obtained at optional purity by appropriately applying known methods for separation and purification, such as concentration, extraction, chromatography, reprecipitation and recrystallization.

The salts of the above-mentioned compound [XV], various intermediates and various isomers thereof can be produced by a known method.

The present invention is described in detail by way of illustrative Examples in the following, to which the invention is not limited.

Examples are shown in a schematic flow in the following.

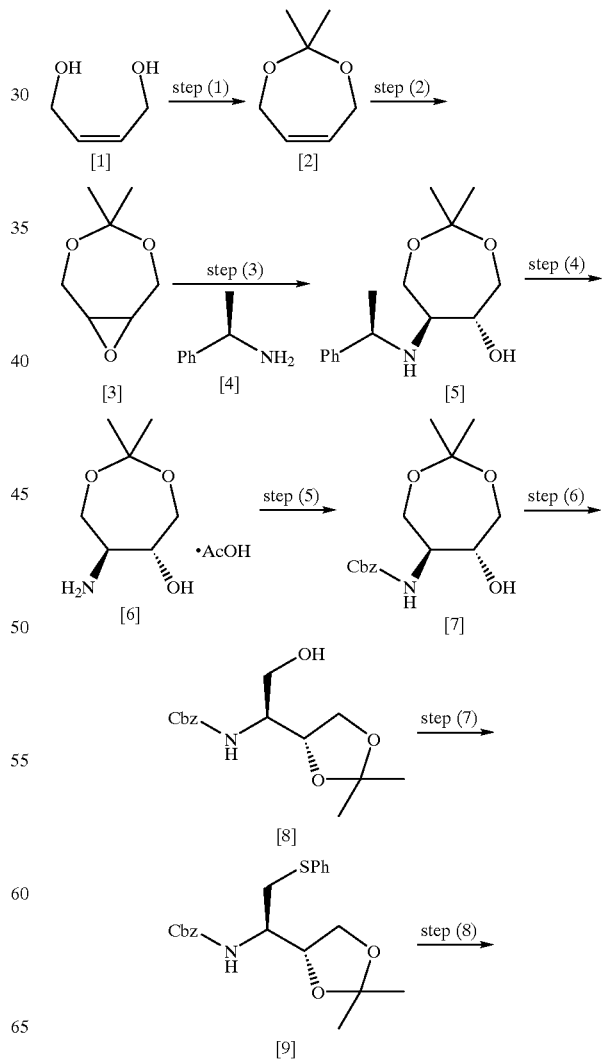

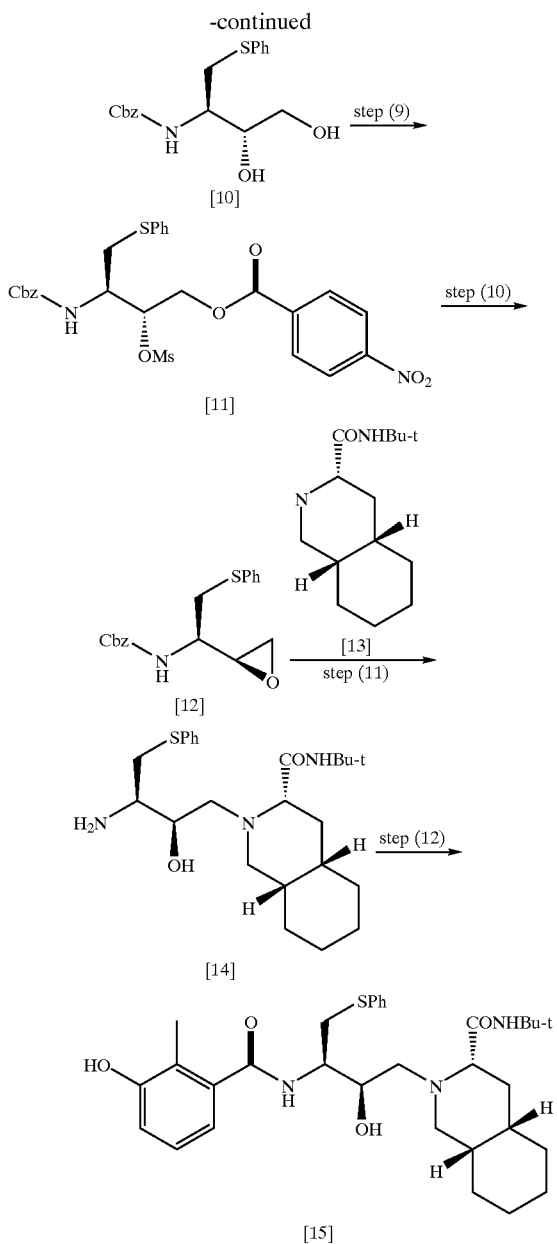

wherein Ph is phenyl, Ac is acetyl, Cbz is benzyloxycarbonyl, Ms is methanesulfonyl and Bu-t is t-butyl.

Reference Example 1: Production of compound [2] (Step 1)

To a mixture of (z)-2-butene-1,4-diol (compound [1], 211.4 g, 2.4 mol) and 2,2-dimethoxypropane (590.2 ml, 4.8 mol) was added p-toluenesulfonic acid monohydrate (30 mg). The solution thus obtained was evaporated under atmospheric pressure to give a colorless transparent liquid of 2,2-dimethyl-4,7-dihydro-1,3-dioxepine (compound [2], 245 g, yield 80%), melting point 140–145° C./760 mmHg. $^1$H-NMR (CDCl$_3$, 300 MHz) δ:5.67 (diffused s, 2H), 4.26 (diffused s, 4H), 1.44 (s, 6H)

Reference Example 2: Production of compound [3] (Step 2)

2,2-Dimethyl-4,7-dihydro-1,3-dioxepine (compound [2], 94.0 g, 0.734 mol), methanol (220 ml) and acetonitrile (116 ml, 2.20 mol) were mixed and the mixture was heated to 60° C. A 30% aqueous hydrogen peroxide solution (208 ml, 1.84 mol) was dropwise added over 1.5 hours at 60–70° C. Simultaneously, an aqueous solution of 1M sodium hydroxide was dropwise added to adjust the reaction system to a pH of 9.1–9.6. Even after the dropwise addition of the aqueous solution of hydrogen peroxide, the dropwise addition of the aqueous solution of 1M sodium hydroxide was continued, during which time the pH was kept at 9.1–9.6 and temperature at 50–70° C., and the mixture was stirred for 1.5 hours. The reaction mixture was cooled to room temperature, diluted with saturated brine (220 ml) and extracted with chloroform (180 ml×1, 90 ml×2). The organic layers were combined, washed with an aqueous solution of sodium hydrogen sulfite (300 ml, 15 g) and dried over magnesium sulfate. The solvent was evaporated and the residue was distilled to give a colorless, transparent liquid of 4,4-dimethyl-3,5,8-trioxabicyclo[5.1.0]octane (compound [3], 86.7 g, yield 82%), melting point 70–74° C./17 mmHg. $^1$H-NMR (CDCl$_3$, 300 MHz) δ:4.08-3.97 (m, 4H), 3.22-3.18 (m, 2H), 1.37 (s, 3H), 1.32 (s, 3H)

Reference Example 3: Production of compound [5] (Step 3)

4,4-Dimethyl-3,5,8-trioxabicyclo[5.1.0]octane (compound [3], 142 g, 0.988 mol) obtained above and (R)-1-phenylethylamine (compound [4], 120 g, 0.988 mol) were dissolved in isopropyl alcohol (400 ml). The mixture was refluxed under heating for 24 hours and concentrated to 366 g. Hexane (400 ml) was added to the residue and the mixture was stirred at 5° C. for one hour. The precipitated crystals were collected by filtration, washed with hexane and dried to give colorless crystals of (5R, 6S)-2,2-dimethyl-6-[(R)-1-phenylethylamino]-1,3-dioxepan-5-ol (compound [5], 94.0 g, yield 36%), melting point 108–108.5° C. $^1$H-NMR (CDCl$_3$, 300 MHz) δ:7.33-7.22 (m,5H), 3.95 (q,1H,J=6.5Hz), 3.75 (dd,1H,J=1.8,12.1Hz), 3.74 (dd,1H,J=2.0,12.5Hz), 3.52 (dd,1H, J=5.5,12.5Hz), 3.48 (ddd,1H,J=0.5,5.9,12.1Hz), 3.37 (dt,1H,J=1.4,5.6Hz), 2.44 (br s,1H), 2.34 (dt,1H,J=1.7,5.5Hz), 1.34 (d,3H,J=6.5Hz), 1.34 (s,3H), 1.31 (s,3H) IR (KBr): 3406, 2590, 1452, 1374, 1219, 1072, 1052, 841, 758, 696 cm$^{-1}$ [α]$_D^{25}$:+91.0° (c1.00, MeOH) Elemental Analysis (C$_{15}$H$_{23}$NO$_3$): Calculated: C,67.90;H, 8.74;N,5.28. Found: C,67.90;H,9.01;N,5.31.

Reference Example 4: Production of compound [6] (Step 4)

20% Palladium hydroxide-carbon (50% wet type, 9.20 g) was suspended in isopropyl alcohol (550 ml), and (5R, 6S)-2,2-dimethyl-6-[(R)-1-phenylethylamino]-1,3-dioxepan-5-ol (compound [5], 92.0 g, 37.7 mmol) and acetic acid (20.8 ml, 37.7 mmol) were added. The mixture was stirred at room temperature under hydrogen atmosphere (3.0 atm) for 8 hours. The catalyst was removed by Celite filtration and the filtrate was concentrated to 105 g. Hexane (400 ml) was added to the residue and the obtained suspension was stirred to allow precipitation of thin crystals. The crystals were collected by filtration and dried to give colorless crystals of (5R, 6S)-6-amino-2,2-dimethyl-1,3-dioxepan-5-ol acetate (compound [6], 76.6 g, yield 100%), melting point 133–134° C. $^1$H-NMR (CDCl$_3$, 300 MHz) δ:3.84 (dd,1H,J=2.5,12.7Hz), 3.74 (dd,1H,J=2.5,12.5Hz), 3.67-3.53 (m,3H), 2.98 (dt,J=2.4,6.5Hz), 1.91 (s,3H), 1.33 (s,6H) IR (KBr): 3178, 2993, 1617, 1561, 1525, 1409, 1385, 1223, 1087, 1031, 846 cm$^{-1}$ [α]$_D^{25}$:+29.6° (c1.05, MeOH) Elemental Analysis (C$_9$H$_{19}$NO$_5$): Calculated: C,48.86;H, 8.66;N,6.33. Found: C,48.98;H,8.70;N,6.36.

EXAMPLE 1

Production of Compound [7] (Step 5)

(5R, 6S)-6-Amino-2,2-dimethyl-1,3-dioxepan-5-ol acetate (compound [6], 29.0 g, 0.131 mol) and sodium hydrogencarbonate (33.0 g, 0.393 mol) were added with stirring to a suspension of water (150 ml) and ethyl acetate (50 ml). A solution of benzyl chloroformate (18.7 ml, 0.131 mol) in ethyl acetate (50 ml) was dropwise added to the mixture with stirring, and the mixture was stirred at room temperature for 6 hours. The organic layer was separated and washed successively with a 0.5 M aqueous citric acid solution (30 ml), a saturated aqueous solution of sodium hydrogencarbonate (30 ml) and saturated brine (30 ml), and dried over magnesium sulfate. The solution was distilled away under reduced pressure to give (5R, 6S)-6-benzyloxycarbonylamino-2,2-dimethyl-5-hydroxy-1,3-dioxepane (compound [7], 38.5 g, yield 99.5%) as a colorless oil. $^1$H-NMR (CDCl$_3$, 300 MHz) δ:7.4-7.3 (m,5H), 5.39 (brd.d,1H), 5.13 (d,J=12.1Hz,1H), 5.07 (d,J=12.1Hz,1H), 3.99 (d,J=12.7Hz,1H), 3.79 (d,J=12.9Hz,1H), 3.8-3.6 (m,2H), 3.57 (m,1H), 3.49 (ddd, J=12.8,2.8,1.8Hz,1H), 2.73 (brd.s,1H), 1.34 (s,3H), 1.32 (s,3H) IR (neat): 3334, 2942, 1703, 1508, 1454, 1376, 1288, 1218, 1157, 1049, 854 cm$^{-1}$ $[\alpha]_D^{25}$:+38.8° (c1.45, MeOH) MS (FAB): m/z 296[M+H]$^+$, Calculated: 296.1501, Found: 296.1498 rational formula: $C_{15}H_{22}NO_5$

EXAMPLE 2

Production of compound [8] (Step 6)

A crude product of (5R, 6S)-6-benzyloxycarbonylamino-2,2-dimethyl-5-hydroxy-1,3-dioxepane (compound [7], 38.5 g) was dissolved in acetone (200 ml) and p-toluenesulfonic acid pyridinium (1.31 g, 5.2 mmol) was added. The mixture was heated at 50–55° C. for 4 hours. After cooling to room temperature, toluene (400 ml) and a saturated aqueous solution of sodium hydrogencarbonate (100 ml) were added. The organic layer was separated and washed successively with a saturated aqueous solution of sodium hydrogencarbonate (100 ml) and water (100 ml). After drying over magnesium sulfate, the residue was concentrated under reduced pressure to give (2S)-2-benzyloxy-carbonylamino-2-[(4R)-2,2-dimethyl-1,3-dioxolan-4-yl]ethanol (compound [8], 36.0 g, yield 94%). $^1$H-NMR (CDCl$_3$, 300 MHz) δ: 7.5-7.2 (m,5H), 5.32 (brd.d,1H), 5.15 (d,J=12.2Hz,1H), 5.09 (d,J=12.2Hz,1H), 4.4-4.3 (m,1H), 4.05 (t,J=7.5Hz,1H), 3.9-3.6 (m,4H), 2.54 (bs,1H), 1.42 (s,3H), 1.35 (s,3H) IR (neat): 3440, 2985, 2938, 2885, 1703, 1530, 1454, 1372, 1250, 1216, 1156, 1069, 856 cm$^{-1}$ $[\alpha]_D^{25}$:-23.5° (c1.02, MeOH) MS (FAB): m/z 296[M+H]$^+$, Found: 296.1491, Calculated: 296.1498 rational formula: $C_{15}H_{22}NO_5$

EXAMPLE 3

Production of Compound [9] (Step 7)

A crude product of (2S)-2-benzyloxycarbonylamino-2-[(4R)-2,2-dimethyl-1,3-dioxolan-4-yl]ethanol (compound [8], 36.0 g) and triethylamine (17.0 ml, 0.122 mol) were dissolved in N,N-dimethylformamide (360 ml), and the mixture was cooled to 4° C. Methanesulfonyl chloride (9.40 ml, 0.122 mol) was dropwise added at 4–12° C., and after the dropwise addition, the mixture was stirred at 4° C. for 30 minutes. Then, potassium carbonate (33.7 g, 0.244 mol) and thiophenol (12.5 ml, 0.122 mol) were successively added under a nitrogen atmosphere, and the mixture was stirred at room temperature for 16 hours. After the completion of the reaction, toluene (500 ml) was added to the mixture. The mixture was washed successively with water (200 ml), a 10% aqueous potassium carbonate solution (150 ml), saturated brine (150 ml), a 0.5 M aqueous citric acid solution (150 ml), a saturated aqueous solution of sodium hydrogen-carbonate (150 ml) and saturated brine (150 ml). After drying over magnesium sulfate, the solvent was distilled away under reduced pressure to give (1R)-1-benzyloxycarbonylamino-1-[(4R)-2,2-dimethyl-1,3-dioxolan-4-yl]-2-phenylthioethane (compound [9], 45.0 g, yield 98%) as an oil. $^1$H-NMR (CDCl$_3$, 300 MHz) δ: 7.5-7.0 (m,10H), 5.2-5.0 (m,3H), 4.50 (td,J=6.9,1.8Hz,1H), 3.99 (m,1H), 3.86 (m,1H), 3.66 (dd, J=8.1,7.0Hz,1H), 3.24 (dd, J=13.8,5.9Hz,1H), 3.04 (dd,J=13.8,8.6Hz,1H), 1.42 (s,3H), 1.30 (s,3H) MS (FAB) m/z 388[M+H]$^+$, Found: 388.1588, Calculated: 388.1583 rational formula: $C_{21}H_{26}NO_4S$

EXAMPLE 4

Production of Compound [10] (Step 8)

A crude product of (1R)-1-benzyloxycarbonylamino-1-[(4R)-2,2-dimethyl-1,3-dioxolan-4-yl]-2-phenylthioethane (45.0 g) was dissolved in methanol (360 ml) and 0.1N hydrochloric acid (90 ml) was added, which was followed by heating for one hour at 80° C. After the reaction mixture was concentrated under reduced pressure, a saturated aqueous solution of sodium hydrogencarbonate (100 ml) and water (50 ml) were added and the mixture was extracted with ethyl acetate (400 mix×2). The obtained organic layers were combined, washed with saturated brine (100 ml) and dried over magnesium sulfate. The solvent was distilled away under reduced pressure to give (2R,3R)-3-benzyloxycarbonylamino-4-phenylthio-1,2-butanediol (compound [10]; 39.0 g, yield 94%) as an oil. $^1$H-NMR (CDCl$_3$, 300 MHz) δ: 7.5-7.0 (m,10H), 5.27 (brd.d,1H), 5.09 (s,2H), 4.01 (m,1H), 3.86 (m,1H), 3.6-3.4 (m,2H), 3.21 (dd, J=13.7,6.7Hz,1H), 3.12 (dd,J=13.7,7.5Hz,1H), 2.62 (brd.d,1H), 2.52 (m,1H)

EXAMPLE 5

Production of Compound [11] (Step 9)

(2R,3R)-3-Benzyloxycarbonylamino-4-phenylthio-1,2-butanediol (compound [10], 39.0 g) and triethylamine (39.1 ml, 0.280 mol) were dissolved in tetrahydrofuran (300 ml) and the mixture was cooled to not more than 5° C. p-Nitrobenzoyl chloride (20.8 g, 0.112 mol) was added to the mixture at 3–10° C., and the mixture was stirred for one hour under ice-cooling. Then, methanesulfonyl chloride (10.4 ml, 0.135 mol) was dropwise added at 2–12° C. and the mixture was stirred under ice-cooling for one hour. After the completion of the reaction, insoluble matter was filtered off and washed with ethyl acetate. The filtrate and the washing were combined and concentrated under reduced pressure. The obtained residue was again dissolved in ethyl acetate (300 ml). This solution was washed successively with water (50 ml), a 0.5 M aqueous citric acid solution (50 ml), a saturated aqueous solution of sodium hydrogencarbonate (50 ml) and saturated brine (50 ml). After drying over magnesium sulfate, the solvent was distilled away under reduced pressure. The obtained residue was recrystallized from toluene (400 ml)/diisopropyl ether (300 ml) to give (2R,3R)-3-benzyloxycarbonylamino-4-phenylthio-2-methanesulfonyloxy-1-(4-nitrobenzoyloxy)butane (compound [11], 38.6 g, yield 51%, from (5R,6S)-6-amino-2,2-dimethyl-5-hydroxy-1,3-dioxepane) as colorless crystals. $^1$H-NMR (CDCl$_3$, 300 MHz) δ: 8.5-8.0 (m,4H), 7.5-7.2 (m,10H), 5.44 (ddd,J=6.9,5.1,2.3Hz,1H), 5.11 (s,2H), 5.09 (brd.d,1H), 4.57 (dd,J=12.0,6.9Hz,1H), 4.50 (dd,J=12.0, 5.1Hz,1H), 4.21 (m,1H), 3.25 (dd,J=14.0,6.2Hz,1H), 3.05 (s,3H), 3.05 (dd,J=14.0,8.2Hz,1H) IR (KBr): 3347, 1725, 1699, 1531, 1514, 1349, 1283, 1172, 1109, 1028, 925 cm$^{-1}$ $[\alpha]_D^{25}$: −14.0° (c1.01, CHCl$_3$) Elemental Analysis (C$_{26}$H$_{26}$N$_2$O$_9$S$_2$): Calculated: C,54.35;H,4.56;N,4.88. Found: C,54.49;H,4.19;N,4.75.

EXAMPLE 6

Production of Compound of [12] (Step 10)

(2R,3R)-3-Benzyloxycarbonylamino-4-phenylthio-2-methanesulfonyl-oxy-1-(4-nitrobenzoyloxy)butane (compound [11], 15.0 g, 26.1 mol) was dissolved in 1,4-dioxane (120 ml) and a 2N aqueous potassium hydroxide solution (28.7 ml, 57.4 mmol) was added. The mixture was stirred for one hour at room temperature and toluene (200 ml) was added. The mixture was washed successively with water (200 ml), a saturated aqueous solution of sodium hydrogencarbonate (200 ml) and saturated brine (100 ml). After drying over magnesium sulfate, the solvent was distilled away under reduced pressure to give (2S, 3R)-3-benzyloxycarbonylamino-4-phenylthio-1-buteneoxide (compound [12], 8.43 g, yield 98%) as a colorless oil. $^1$H-NMR (CDCl$_3$, 300 MHz) δ: 7.5-7.1 (m,10H), 5.2-5.0 (m,3H), 3.70 (m,1H), 3.22 (d,J=5.6Hz,2H), 2.99 (m,1H), 2.9-2.6 (m,2H) IR (KBr): 3302, 1694, 1538, 1323, 1256, 1100, 1028, 1006, 882 cm$^{-1}$ $[\alpha]_D^{25}$: −26.2° (c1.01, CHCl$_3$) Elemental Analysis (C$_{18}$H$_{19}$NO$_3$S): Calculated: C,65.63;H, 5.81;N,4.25. Found: C,65.36;H,5.85;N,4.33.

EXAMPLE 7

Production of Compound [14] (Step 11)

A crude product of (2S, 3R)-3-benzyloxycarbonylamino-4-phenylthio-1-buteneoxide (compound [12], 8.43 g) and (3S, 4aS, 8aS)-decahydroisoquinoline-3-carboxylic acid t-butylamide (compound [13], 4.98 g, 20.9 mmol) were dissolved in isopropyl alcohol (70 ml), and the mixture was heated at 70–75° C. for 5 hours. Then, a 2N aqueous potassium hydroxide solution (52.3 ml, 104.5 mmol) was added and the mixture was further heated at 70–75° C. for 15 hours. After cooling to room temperature, toluene (120 ml) was added and the mixture was washed with water (120 ml). The organic layer was extracted with 1N hydrochloric acid (80 ml×1, 40 ml×1) and the aqueous solutions obtained were combined and washed with toluene (100 ml×3). This aqueous solution was adjusted to pH 12 with a 5N aqueous potassium hydroxide solution and extracted with toluene (120 ml). The organic layer was washed with saturated brine. After drying over magnesium sulfate, the solvent was distilled away under reduced pressure to give (3S, 4aS, 8aS)-2-((2R, 3R)-3-amino-2-hydroxy-4-phenylthiobutyl)-decahydroisoquinoline-3-carboxylic acid t-butylamide (compound [14], 9.39 g, yield 85%) as a colorless oil. $^1$H-NMR (CDCl$_3$, 300 MHz) δ: 7.5-7.1 (m,5H), 6.05 (brd.s, 1H), 3.68 (m,1H), 3.37 (dd,J=13.0,2.8Hz,1H), 3.02-2.88 (m,2H), 2.83 (dd, J=13.0,9.8Hz,1H), 2.64 (dd,J=13.2,5.1Hz, 1H), 2.60 (dd,J=8.0,3.7Hz,1H), 2.30 (dd,J=13.2,6.6Hz,1H), 2.27 (dd,J=11.8,3.3Hz,1H), 1.32 (s,9H), 2.0-1.0 (m,12H)

EXAMPLE 8

Production of Compound [15] (Step 12)

(3S, 4aS, 8aS)-2-((2R, 3R)-3-Amino-2-hydroxy-4-phenylthiobutyl)-decahydroisoquinoline-3-carboxylic acid t-butylamide (compound [14], 9.39 g) and sodium hydrogencarbonate (4.55 g, 54.2 mmol) were added to a suspension of water (40 ml) and ethyl acetate (40 ml). A solution of 3-acetoxy-2-methylbenzoyl chloride (4.37 g, 20.6 mmol) in ethyl acetate (40 ml) was dropwise added to the suspension with stirring under ice-cooling. The mixture was further stirred for one hour under ice-cooling and water (20 ml) was added. The organic layer was separated and washed with a saturated aqueous solution (20 ml) of sodium hydrogencarbonate. After drying over magnesium sulfate, the solvent was distilled away under reduced pressure to give (3S, 4aS, 8aS)-2-[(2R, 3R)-3-(3-acetoxy-2-methylbenzoylamino)-2-hydroxy-4-phenylthiobutyl]decahydroisoquinoline-3-carboxylic acid t-butylamide (12.7 g, yield 96%) as colorless amorphous. $^1$H-NMR (CDCl$_3$, 300 MHz) δ: 7.5-7.1 (m,8H), 7.1-7.0 (m,1H), 5.51 (brd.s,1H), 4.48 (m,1H), 4.07 (m,1H), 3.81 (dd,J=13.7,9.2Hz,1H), 3.41 (dd,J=13.7,4.7Hz,1H), 2.91 (dd,J=11.7,2.0Hz,1H), 2.56 (dd, J=12.9,9.1Hz,1H), 2.44 (m,1H), 2.32 (s,3H), 2.27 (s,3H), 2.3-2.1 (m,2H), 1.99 (m,1H), 1.9-1.1 (m,11H), 1.07 (s,9H)

The obtained (3S, 4aS, 8aS)-2-[(2R, 3R)-3-(3-acetoxy-2-methyl-benzoylamino)-2-hydroxy-4-phenylthiobutyl]decahydroisoquinoline-3-carboxylic acid t-butylamide (12.7 g) was dissolved in methanol (96 ml) and 28% aqueous ammonia (24 ml) was added, which was followed by stirring for 1.5 hours. The resulting precipitate was collected by filtration and washed with a mixed solution of methanol (75 ml)/water (25 ml). The residue was dried at 50° C. under reduced pressure to give (3S, 4aS, 8aS)-2-[(2R, 3R)-2-hydroxy-3-(3-hydroxy-2-methylbenzoylamino)-4-phenylthiobutyl]decahydroisoquinoline-3-carboxylic acid t-butylamide (compound [15], 8.00 g, yield 54%, from (2R, 3R-benzyloxycarbonylamino-4-phenylthio-2-methanesulfonyloxy-1-(4-nitrobenzoyloxy)butane) as colorless crystals. $^1$H-NMR (CD$_3$OD, 300 MHz) δ: 7.49 (m,2H), 7.27 (m,2H), 7.17 (m,1H), 7.01 (m,1H), 6.90 (m,1H), 6.79 (m,1H), 4.43 (m,1H), 4.06 (m,1H), 3.54 (dd,J=10.1,3.5Hz, 1H), 3.37 (m,1H), 3.04 (dd,J=8.7,1.7Hz,1H), 2.60 (m,2H), 2.24 (s,3H), 2.17 (m,2H), 2.01 (m,1H), 1.9-1.1 (m,11H), 1.17 (s,9H)

EXAMPLE 9

Production of Methanesulfonate of Compound [15]

(3S, 4aS, 8aS)-2-[(2R, 3R)-2-Hydroxy-3-(3-hydroxy-2-methyl-benzoylamino)-4-phenylthiobutyl]decahydroisoquinoline-3-carboxylic acid t-butylamide (compound [15], 7.80 g, 13.7 mmol) was suspended in tetrahydrofuran (40 ml) and methanesulfonic acid (0.918 ml, 14.1 mol) was added, which was stirred until the solid was completely dissolved. The mixture was dropwise added to methyl-t-butyl ether (470 ml) (after rinsing with 5 ml of tetrahydrofuran). Precipitate was produced instantaneously with the dropwise addition. The mixture was stirred at room temperature for 2 hours after the dropwise addition. The precipitate was collected by filtration, washed with methyl-t-butyl ether (27 ml) and dried at 65° C. for one day under reduced pressure to give (3S, 4aS, 8aS)-2-[(2-R, 3R)-2-hydroxy-3-(3-hydroxy-2-methylbenzoylamino)-4-phenylthiobutyl]decahydroisoquinoline-3-carboxylic acid t-butylamide methanesulfonate (8.68 g, yield 95%) as a colorless solid. $^1$H-NMR (CD$_3$OD, 300 MHz) δ: 7.93 (brd.s, 1H), 7.43 (m,1H), 7.30 (m,2H), 7.22 (m,1H), 7.03 (t,J= 5.9Hz,1H), 6.86 (m,2H), 4.19 (m,1H), 4.08 (m,1H), 3.61 (dd,J=9.7,1.3Hz,1H), 3.45 (dd,J=10.4,2.6Hz,1H), 3.38 (dd, J=9.8,2.9Hz,1H), 3.28 (m,1H), 3.17 (m,1H), 3.05 (dd, J=10.4,7.7Hz,1H), 2.68 (s,3H), 2.26 (s,3H), 2.2-2.1 (m,12H), 1.30(s,9H) The production method of the present invention is extremely easy and simple as compared to the conventional methods, and enables effective production of compound [XV] at high yields, which includes compound

[XVI] having an HIV protease inhibitory action. In addition, the novel intermediates of the present invention are extremely useful as intermediates for producing not only the aforementioned compound [XVI] but also compounds useful as X-ray contrast media such as the compounds for X-ray image development as described in U.S. Pat. No. 4,439,613.

What is claimed is:

1. A (5R,6S)-6-substituted amino-1,3-dioxepan-5-ol derivative of the formula (VII)

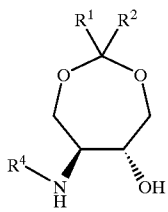

(VII)

wherein $R^1$ and $R^2$ are the same or different and each is a hydrogen atom, an alkyl or an aryl, or $R^1$ and $R^2$ combinedly form a cycloalkyl ring together with the adjacent carbon atom, and $R^4$ is an amino-protecting group selected from the group consisting of an optionally substituted aralkylidene, an optionally substituted aralkyl, an optionally substituted acyl which is selected from the group consisting of formyl, acetyl, propionyl, butyryl, pivaloyl, 2-chloroacetyl, 2-bromoacetyl, 2-iodoacetyl, 2,2-dichloroacetyl, 2,2,2-trichloroacetyl, 2,2,2-trifluoroacetyl, phenylacetyl, phenoxyacetyl, benzoyl, 4-chlorobenzoyl, 4-methoxybenzoyl, 4-nitrobenzoyl, naphthylcarbonyl and adamantylcarbonyl, an optionally substituted alkenyloxycarbonyl, phenyloxycarbonyl, an optionally substituted aralkyloxycarbonyl, an optionally substituted lower alkylsilyl, an optionally substituted alkylthiocarbonyl, an optionally substituted aralkylthiocarbonyl, an optionally substituted phosphoryl and an optionally substituted phosphinyl, an enantiomer thereof or a salt thereof.

* * * * *